US012653493B2

(12) United States Patent
Olivier

(10) Patent No.: US 12,653,493 B2
(45) Date of Patent: Jun. 16, 2026

(54) CARDIAC IMAGE ANALYSIS

(71) Applicant: KONINKLIJKE PHILIPS N.V., Eindhoven (NL)

(72) Inventor: Antoine Olivier, Suresnes (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 165 days.

(21) Appl. No.: 18/289,967

(22) PCT Filed: May 12, 2022

(86) PCT No.: PCT/EP2022/062971
§ 371 (c)(1),
(2) Date: Nov. 8, 2023

(87) PCT Pub. No.: WO2022/243178
PCT Pub. Date: Nov. 24, 2022

(65) Prior Publication Data
US 2024/0293100 A1      Sep. 5, 2024

(30) Foreign Application Priority Data

May 21, 2021    (EP) ..................................... 21290031

(51) Int. Cl.
*A61B 8/08*        (2006.01)
*A61B 8/00*        (2006.01)
*G06T 7/00*        (2017.01)

(52) U.S. Cl.
CPC .......... *A61B 8/0883* (2013.01); *A61B 8/5223* (2013.01); *A61B 8/543* (2013.01);
(Continued)

(58) Field of Classification Search
CPC ..... A61B 8/0883; A61B 8/5223; A61B 8/543; A61B 8/5284; G06T 7/0012; G06T 2207/10132; G06T 2207/30048
See application file for complete search history.

(56) References Cited

U.S. PATENT DOCUMENTS

2010/0240996 A1    9/2010  Ionasec et al.
2017/0007201 A1*   1/2017  Kobayashi ........... A61B 6/5217
(Continued)

FOREIGN PATENT DOCUMENTS

EP        3494893 A1     6/2019
EP        3571999 A1    11/2019
(Continued)

OTHER PUBLICATIONS

International Search Report and Written Opinion for PCT/EP2022/062971; Mailing date: Jul. 11, 2022, 13 pages.
(Continued)

*Primary Examiner* — Siamak Harandi

(57) ABSTRACT
An automated method for selecting image frames from a sequence of image frames for application of one or more anatomical/physiological assessment or quantification algorithms. In particular, the method is based on classifying a received sequence of image frames in accordance with an imaging view from which a sequence of image frames has been acquired. The method further includes determining for each frame in the sequence a sub-phase of the image frame within a cardiac cycle of the imaged heart of the subject. These determined parameters are used to identify one or more suitable frames for application of one or more predetermined algorithms, and/or can be used to identify one or more suitable algorithms for application to each, or a subset, of the frames.

14 Claims, 2 Drawing Sheets

(52) U.S. Cl.
   CPC .. *G06T 7/0012* (2013.01); *G06T 2207/10132* (2013.01); *G06T 2207/30048* (2013.01)

(56)                References Cited

U.S. PATENT DOCUMENTS

| | | | | |
|---|---|---|---|---|
| 2019/0076127 | A1* | 3/2019 | Aase | A61B 8/463 |
| 2019/0388064 | A1 | 12/2019 | Kezurer et al. | |
| 2022/0319006 | A1* | 10/2022 | Annangi | G06N 3/047 |

FOREIGN PATENT DOCUMENTS

| | | | |
|---|---|---|---|
| JP | 2016002438 | * | 1/2016 |
| JP | 6874199 B1 | | 5/2021 |
| WO | 2020028125 A1 | | 2/2020 |

OTHER PUBLICATIONS

Ghorbani, A. et al., "Deep learning interpretation of echocardiograms", npj Digital Medicine, 2020, vol. 3, Article No. 10, 10 pages.

Dezaki, F. et al., "Deep Residual Recurrent Neural Networks for Characterisation of Cardiac Cycle Phase from Echocardiograms", Deep Learning in Medical Image Analysis and Multimodal Learning for Clinical Decision Support, 2017, 9 pages.

Dezaki, F. et al., "Cardiac Phase Detection in Echocardiograms With Densely Gated Recurrent Neural Networks and Global Extrema Loss", IEEE Transactions on Medical Imaging, 2019, vol. 38, No. 8, pp. 1821-1832.

Ouyang, D. et al., "Video-based AI for beat-to-beat assessment of cardiac function", Nature, 2020, vol. 580, pp. 252-256.

Gaibazzi, N. et al., "Cardiac calcium score on 2D echo: correlations with cardiac and coronary calcium at multi-detector computed tomography", Cardiovasc Ultrasound, 2014, vol. 12, 9 pages.

Gillis, K. et al., "Clinical validation of an ultrasound quantification score for aortic valve calcifications", International Journal of Cardiology, 2018, vol. 252, pp. 68-71.

* cited by examiner

10

Receive cardiac U/S image sequence ~ 12

Determine view of images ~ 14

Determine phase point of each frame ~ 16

Apply cardiac assessment algorithm(s) to selected frames based on view and phase ~ 18

Generate data output ~ 20

Ultrasound imaging apparatus ~ 42

32

I/O ~ 34

40

Proc ~ 36

UI ~ 44

CARDIAC IMAGE ANALYSIS

CROSS-REFERENCE TO PRIOR APPLICATIONS

This application is the U.S. National Phase application under 35 U.S.C. § 371 of International Application No. PCT/EP2022/062971, filed on May 12, 2022, which claims the benefit of European Patent Application No. 21290031.0, filed on May 21, 2021. These applications are hereby incorporated by reference herein.

FIELD OF THE INVENTION

The present invention relates to a method for cardiac image analysis, in particular for assessment of a heart valve.

BACKGROUND OF THE INVENTION

Heart valve disorders are a major class of cardiac pathology. These can be assessed using ultrasound imaging. Diagnosis typically requires a long examination, with manual assessment by a clinician.

Aortic valve diseases are amongst the most widespread cardiac valve diseases. For instance, the prevalence of aortic stenosis in developed countries is 3%.

Aortic stenosis can be assessed from US images using Doppler echocardiographic parameters such as maximum transaortic jet velocity, mean transaortic pressure gradient, or aortic valve area. These can be deduced from a continuity equation.

Aortic calcification is currently assessed using computed tomography, and the resulting Agatston score is the gold standard.

Mitral valve disease is also a major class of heart valve pathology. Mitral valve disease can include mitral valve stenosis or mitral valve regurgitation. Mitral valve disease can be assessed using ultrasound imaging. For example, ultrasound imaging from the apical four chamber view enables assessment of mitral valve area, which permits detection of mitral valve stenosis.

It has previously been proposed to perform such exams automatically or semi-automatically using ultrasound. However, all known approaches require that a user selects an adequate frame before automatic assessment is applied. For instance, quantification of a particular parameter may require that the ultrasound image(s) capture a correct view, e.g. parasternal short axis (PSAx) or parasternal long axis (PLAx). It may also require one or a series of image frames which span a particular portion of the heart cycle.

US 2017/007201 A1 discloses an ultrasonic diagnostic apparatus including processing circuitry. The processing circuitry is configured to extract an edge of a mitral valve based on 3D images generated by image generating circuitry, track the edge of the mitral valve, determine a timing of end-systole, and calculate a gap between valve leaflets based on a 3D image of the frame corresponding to end-systole.

EP 3,571,999 A1 discloses an ultrasound diagnostic apparatus including processing circuitry. The processing circuitry is configured to specify a region being part of a heart on the basis of moving image data rendering the heart, and obtain a reference waveform that makes it possible to estimate a cardiac phase on the basis of the region in the moving image data.

SUMMARY OF THE INVENTION

The invention is defined by the claims.

According to examples in accordance with an aspect of the invention, there is provided a method comprising: receiving a temporal sequence of ultrasound frames of a heart of a subject, spanning at least one heart cycle; determining a view represented by the sequence of frames; determining for each frame a phase point of the frame within a cardiac cycle, the phase point being a sub-phase point of one of systole or diastole phases; applying one or more cardiac valve analysis algorithms, each algorithm configured to receive one or more input ultrasound frames representative of the heart in a pre-defined one or more views, and at a pre-defined one or more phase points of the cardiac cycle, wherein the one or more input image frames provided to each algorithm are selected based on the determined view and phase point of each of the received frames; and generating a data output representative of an output of each of the one or more algorithms.

Embodiments of the invention provide a method for performing an automated cardiac valve (e.g. aortic valve) assessment based on a sequence of ultrasound frames.

By detecting the view represented by the image series, and classifying each frame according to a phase interval within which it lies, appropriate image frames can automatically be supplied as inputs to appropriate assessment algorithms, permitting cardiac valve assessment. More particularly, by detecting for each frame a sub-phase (being a subsidiary portion of one of systole or diastole) of the frame, this permits more precise control over which frames are supplied to which algorithms.

The ultrasound image frames may be received from an ultrasound imaging apparatus, and wherein the method is performed in real time with image acquisition by the imaging apparatus. In other examples, the image sequence may be received from a datastore, so that the method is performed offline based on image data from an earlier imaging session.

The determined phase point may correspond to one of a set of pre-determined phase intervals, each phase interval being a sub-interval of one of systole and diastole phases.

In some embodiments, the pre-determined phase intervals may comprise at least a subset of: Isovolumetric relaxation, Ventricular filling, Atrial contraction, Isovolumetric contraction, and Ventricular ejection.

In some examples, at least one of the algorithms may be adapted to receive a sequence of image frames. Optionally, the method may comprise selecting from the received image frames a temporally consecutive subset of the image frames based on the phase points of the frames. For example, a temporally consecutive subset of the image frames spanning one of the phase intervals may be selected.

In some embodiments, the method may further comprise detecting within each frame a motion state of one or more anatomical features, each of the one or more anatomical features having a cyclical motion pattern over a cardiac cycle. The determining of the phase point of each frame may be based on the detected motion state of the one or more anatomical features.

The determining the view may comprise classifying the view as one of a set of pre-defined views, and wherein the pre-defined views include one or more of: parasternal short axis (PSAx) view, parasternal long axis (PLAx) view, apical four chamber view, apical two chamber view, and apical long axis view.

Parasternal short axis (PSAx) view, and parasternal long axis (PLAx) view are particularly valuable for examination of the aortic valve. Apical views are particularly valuable for examining the mitral valve. For example, the mitral valve area can be assessed from the apical four chamber view.

In some embodiments, each of at least a subset of the one or more analysis algorithms may be adapted to output a parameter of the aortic valve and/or of the mitral valve.

In some embodiments, the one or more analysis algorithms may be adapted to output an assessment indicator for one or more of: aortic stenosis (AS), aortic valve area (AVA), aortic valve calcification, mitral valve area, and mitral or aortic valve leaflet count.

In some embodiments, the method may further comprise receiving an ECG signal for the subject. The determining of the phase point for each frame may be further based on the ECG signal.

The waveform of a subject's ECG signal is closely linked with the cardiac cycle. For instance, the QRS pattern starts just before ventricular contraction. The P-wave and the T-wave are related to atrial polarization and ventricle repolarization respectively, and are therefore closely linked to the phases of the heart. Therefore, if an ECG signal is available, it may be provided as an additional input to the phase classifier, improving accuracy of the phase point detection.

The one or more anatomical features detected or tracked in each image frame may include the aortic valve, the mitral valve and/or at least a portion of a ventricle or atrium of the heart.

In some embodiments, determining the phase point, and/ or determining the view is based on use of an artificial intelligence (AI) algorithm, for example a machine learning algorithm.

In some embodiments, the determining the phase point and/or determining the view may be based on use of a deep neural network (DNN).

In some embodiments, the determining the phase point and/or determining the view may be based on use of a recurrent neural network (RNN).

Compared to a classical DNN, where only the spatial structure of the image is analyzed, RNN and spatio-temporal networks are able to analyze the temporal relationships between consecutive frames in a sequence. This enhances accuracy of the phase detection.

In some embodiments, the method may further comprise generating a display output for causing a user interface to simultaneously display one or more of the image frames and the determined phase point for the frame.

By displaying the determined phase points for each frame, a user can review and check the accuracy of the determination.

Optionally, the method may further comprise receiving a user input from the user interface indicative of a user modification of the cardiac phase point of one or more of the image frames. Hence here, the user may manually override the automatic phase determinations.

Examples in accordance with a further aspect of the invention provide a computer program product comprising code means configured, when executed on a processor, to cause the processor to perform a method in accordance with any example or embodiment outlined above or described below, or in accordance with any claim of this application.

Examples in accordance with a further aspect of the invention provide a processing arrangement comprising: an input/output; and one or more processors. The one or more processors are adapted to: receive at the input/output a temporal sequence of ultrasound frames of a heart of a subject, spanning at least one heart cycle; determine a view represented by the sequence of frames; determine for each frame a phase point of the frame within a cardiac cycle, the phase point being a sub-phase of one of systole or diastole phases; apply one or more cardiac valve analysis algorithms, each algorithm configured to receive one or more input ultrasound frames representative of the heart in a pre-defined one or more views, and at a pre-defined one or more phase points of the cardiac cycle, wherein the one or more input image frames provided to each algorithm is selected based on the determined view and phase point of each of the received frames; and generate a data output representative of an output of each of the one or more algorithms.

As described previously, in some embodiments, the phase point may corresponds to one of a set of pre-determined phase intervals, each phase interval being a sub-interval of one of systole and diastole phases.

As described previous, in some embodiments, the processing arrangement may further be adapted to detect within each frame a motion state of one or more anatomical features, each of the one or more anatomical features having a cyclical motion pattern over a cardiac cycle. The determining of the phase point of each frame may be based on the detected motion state of the one or more anatomical features.

Examples in accordance with a further aspect of the invention provide a system comprising: a processing arrangement in accordance with any example or embodiment outlined above or described below, or in accordance with any claim of this application; an ultrasound imaging apparatus adapted to output ultrasound image data to the processing arrangement; and a user interface comprising a display, operatively coupled with the processing arrangement.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
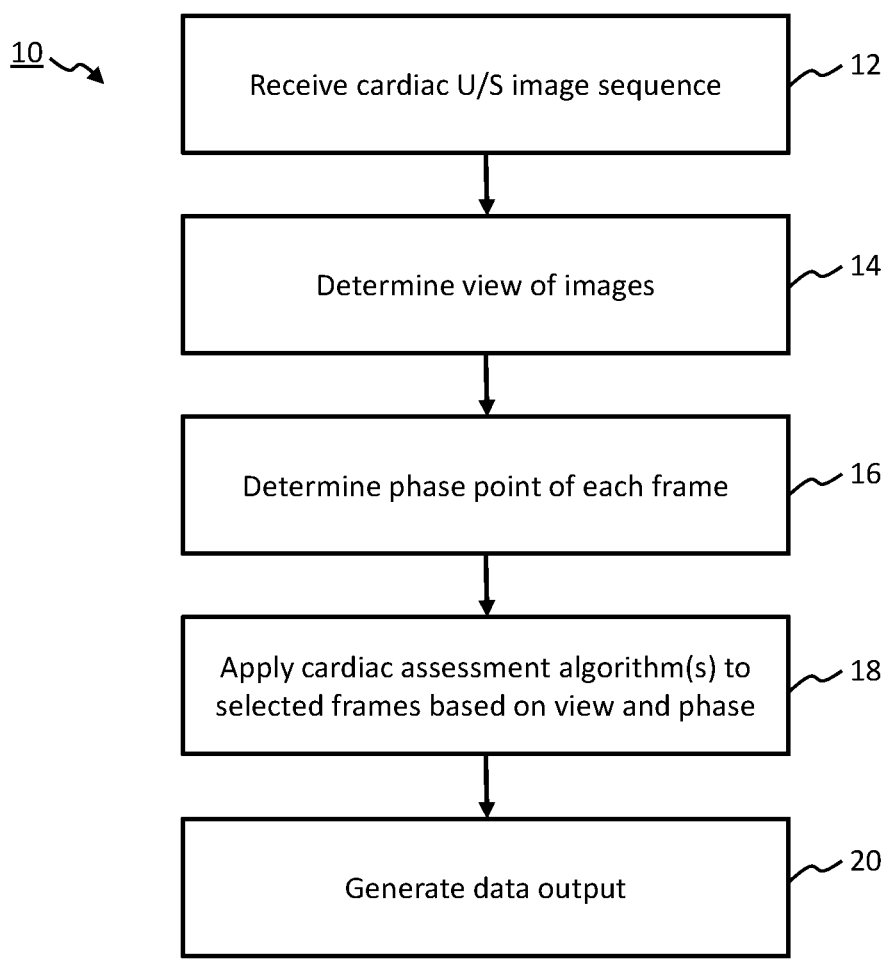
FIG. 1 shows steps of an example method according to one or more embodiments.

The invention will be described with reference to the Figs.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figs. are merely schematic and are not drawn to scale. It should also be understood that the same reference numerals are used throughout the Figs. to indicate the same or similar parts.

The invention provides an automated method for selecting image frames from a sequence of image frames for application of one or more anatomical/physiological assessment or quantification algorithms. In particular, the method is based on classifying received sequence of image frames in accordance with an imaging view from which a sequence of image frames has been acquired. The method further includes determining for each frame in the sequence a sub-phase of the image frame within a cardiac cycle of the imaged heart of the subject. These determined parameters are used to identify one or more suitable frames for application of one or more predetermined algorithms, and/or can be used to identify one or more suitable algorithms for application to each, or subset, of the frames.

Embodiments of the invention are particularly applicable for assessment of heart valves and heart valve disease, for example the aortic valve or mitral valve.

Embodiments of the invention facilitate (i) automatically classifying a view of the imaged heart represented in an image sequence and (ii) automatically identifying for the ultrasound image sequence (covering one or several cardiac cycles) the various phases of the cardiac cycles. This removes from an operator the burden of performing these steps manually, and the need to manually select a frame suitable for application of one or more assessment algorithms. This results in a fully automated workflow, wherein an ultrasound sequence is communicated to a system or processor, and, depending upon the view represented by the sequence, and the phases of the cardiac cycle included in the sequence, a comprehensive assessment of one or more anatomical features, e.g. the aortic or mitral valve, is produced. All steps of the method may be performed by a standalone processing arrangement, by a computer system comprising a processing arrangement, and/or by a processing arrangement comprised by an ultrasound imaging system, e.g. a cart-based ultrasound imaging system. The steps of the method may be performed on-line (in real time) during an ultrasound scanning session, or may be performed offline, for instance using a processor of a computer.

Any herein described method may be a computer-implemented method.

An advantage of certain embodiments of the present invention is the capacity to identify different pre-defined sub-sequences, within the overall sequence of images, for instance isolating a sub-sequence of image frames corresponding to one of the phases or sub-phases of the heart cycle.

FIG. 1 outlines steps of an example method, for implementation by a computer or processor, in accordance with embodiments of the present invention.

The method 10 comprises receiving 12 a temporal sequence of ultrasound frames of a heart of a subject, spanning at least one heart cycle. This may comprise a sequence of 2D ultrasound images. These may be B-mode ultrasound images for example. The sequence may span a plurality of heart cycles. The image sequence may be received from an ultrasound imaging system in real time with ultrasound scanning, or received from a datastore.

The method 10 further comprises determining 14 a view represented by the sequence of frames. A view represented by the sequence of frames depends on a viewing position and direction (i.e. a position and orientation of an ultrasound device) used to acquire the sequence of frames, and may be defined in terms of the anatomical structures captured in the frames and the configuration of these anatomical structures in the frames.

The view represented by the sequence of frames may be selected from a set of predefined views, such as a set of standard cardiac views. Standard cardiac views include the parasternal short axis (PSAx) view, the parasternal long axis (PLAx) view, the apical four chamber view, the apical two chamber view, and the apical long axis view. Many anatomical/physiological assessments require images corresponding to a particular anatomical view. For instance, a parasternal short axis (PSAx) image is needed for an ultrasound-based assessment of aortic valve calcification, while computation of an aortic valve area from a continuity equation requires a parasternal long axis (PLAx) image.

The method 10 further comprises determining 16 for each frame a phase point of the frame within a cardiac cycle, the phase point being a sub-phase point of one of systole or diastole phases.

In some embodiments, the method 10 comprises detecting within each frame of the sequence a motion state of one or more anatomical features, each of the one or more anatomical features having a cyclical motion pattern over a cardiac cycle, and wherein the detection of the phase point is based on the detected motion state of the one or more anatomical features. The one or more anatomical features may for example include one or more heart chambers (e.g. left/right ventricle) or one or more heart valves. The motion state may include a state of expansion/contraction of the anatomical features, for example an expansion or contraction state of a heart chamber such as the left/right ventricle. In other examples, the movement state may comprise a positioning of a heart valve, such as the aortic or mitral valve.

The method 10 further comprises applying 18 one or more cardiac valve analysis/assessment algorithms, each algorithm configured to receive one or more input ultrasound frames representative of the heart in a pre-defined one or more views, and at a pre-defined one or more phase points of the cardiac cycle. The method comprises selecting one or more input image frames to be provided to at least a subset of the algorithms based on the determined view and phase point of each of the received frames. The one or more analysis or assessment algorithms may be stored on a datastore and retrieved for use during the method. The view and phase point requirements for input image frames of each algorithm may be stored as metadata associated with each algorithm in the datastore. The method may comprise reading this metadata to identify the input image frame requirements for each algorithm. The one or more algorithms may be automatically triggered responsive to completion of preceding steps of the method.

The method further comprises generating 20 a data output representative of an output of each of the one or more algorithms. This output may be communicated to a further system or device, for example to a remote computer, or to a local or remote datastore. The communication of the data output may be performed using a communication module or input/output module.

In some embodiments, the method may comprise generating a display output for controlling a display device of a user interface to visually present the sequence of ultrasound image frames, along with the detected phase of each image frame.

In some embodiments, the user interface may permit verification and/or correction of the phase of each frame by a user, for example allowing the user to adjust a time interval between the various sub-phases. This may be performed in advance of subsequent application of the one or more analysis or assessment algorithms. For example, the method may pause pending input by the user at the user interface.

7                                                                              8

Figure 2:
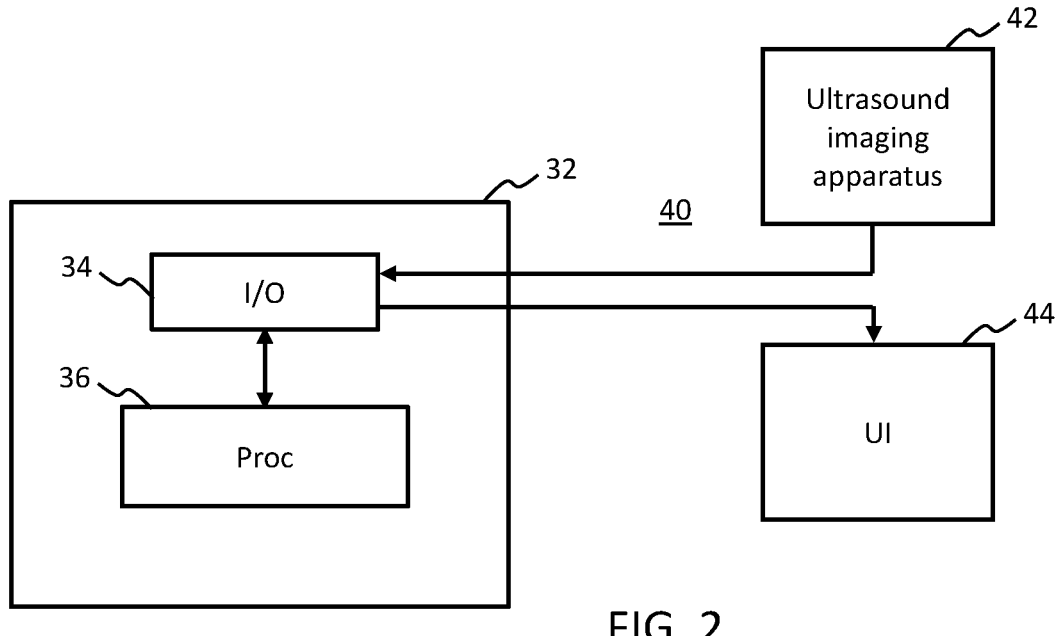
FIG. 2 shows a system comprising a processing arrangement in accordance with one or more embodiments.

As schematically illustrated in FIG. 2, a further aspect of the invention provides a processing arrangement comprising an input/output (I/O) 34; and one or more processors 36 configured to perform the method outlined above, or in accordance with any embodiment disclosed above or described below, or in accordance with any claim of this application.

A further aspect of the invention provides a system 40 comprising the processing arrangement 32 as described above, and further comprising an ultrasound imaging apparatus 42 adapted to output ultrasound image data to the processing arrangement, this data being received at the input/output 34. The system may optionally further include a user interface 44 comprising a display, operatively coupled with the processing arrangement.

As described above, one of the steps of the method comprises determining, for each frame within the image sequence, a sub-phase of the cardiac cycle to which the frame belongs. Details for implementing this step we will now be outlined.

The determined phase point for each frame preferably corresponds to one of a set of pre-determined phase intervals, each phase interval being a sub-interval of one of systole and diastole phases.

In particular, a cardiac cycle can be understood as comprising a sequence of five major phase intervals, each corresponding to a sub-phase of the heart cycle, and may be summarized as follows.

Isovolumetric relaxation: during this phase interval, blood flows back to the atria.

Ventricular filling: during this phase interval, the atrio-ventricular valves open, and blood begins flowing from the atria to the ventricles.

Atrial contraction: the atria contract, and blood continues filling the ventricles. This is the end of the diastole phase.

Isovolumetric contraction: the ventricles contract, while the aortic and pulmonary valves remain closed. This is the beginning of the systole phase. Blood is not yet flowing through the aorta and pulmonary artery.

Ventricular ejection: the aortic and pulmonary valves open, and blood is ejected to the rest of the body.

The aortic valve is closed during the first four of the phase intervals, and opened during the fifth. These sub-phases of the heart cycle, and the corresponding aortic valve state for each, are summarized in Table 1 below.

TABLE 1

| Diastole | Isovolumetric relaxation | Aortic valve closed |
|----------|--------------------------|---------------------|
|          | Ventricular filling      | Aortic valve closed |
|          | Atrial contraction       | Aortic valve closed |
| Systole  | Isovolumetric contraction | Aortic valve closed |
|          | Ventricular ejection     | Aortic valve open   |

The detection of the phase point of each image frame can be performed using an AI algorithm such as a machine learning algorithm. Deep neural networks (DNN) are well suited to detection of the phase point. However, classical image processing techniques may additionally or alternatively be used.

As described above, the method comprises determining for the received image sequence a view of the heart which is represented by the sequence.

Determining the view may comprise classifying the view as one of a set of pre-defined views, and wherein the pre-defined views may include one or more of: parasternal short axis (PSAx) view, parasternal long axis (PLAx) view, apical four chamber view, apical two chamber view, and apical long axis view.

For example, where the method is for analysis or assessment of the aortic valve, the step of determining the view may comprise classifying the view as one of: parasternal short axis (PSAx) view, and parasternal long axis (PLAx) view. Where the method is for assessment or analysis of the mitral valve, the step of determining the view may comprise classifying the view as one of: the apical four chamber view, the apical two chamber view, and the apical long axis view.

Detection of a view of the image sequence can be performed using an AI algorithm such as a machine learning algorithm. For example, a neural network may be applied, the neural network adapted to receive as input one or more of the images of the sequence, and adapted to generate a data output indicative of a predicted view of the images of the sequence. A deep neural network (DNN) may be used in some examples. The machine learning algorithm may receive the full image sequence or may receive only one, or a subset, of the sequence of images. The latter option may be preferred since it enables application of the method in real-time with image acquisition, where the full sequence of images is not available at the start of the method. Even where the full image sequence is available, the algorithm may be trained to receive only one or a subset of the images, e.g. randomly selected frames of the sequence. The machine learning algorithm may be trained in advance based on a training dataset comprising previously acquired image frames of the heart in different of the set of pre-determined standard views, and each being manually labelled according to the view it represents. The machine learning algorithm may be a classifier algorithm, adapted to output a classification of an input image frame according to the view represented in the image frame.

As mentioned above, the determination of the phase point of each of the image frames may be performed by an AI algorithm, e.g. a machine learning algorithm. In some embodiments, the machine learning algorithm may be adapted to receive as input the full image sequence spanning one or more cardiac cycles, and to output a label or tag for each frame in the sequence indicative of the phase point to which the frame corresponds. This option may lead to greater accuracy in the phase identification since the algorithm is able to take into account the contextual information provided by the image frames preceding and following each frame of the series. In other examples, the algorithm may be adapted to receive as input only a single image frame at a time and to generate an output indicative of a phase point of the image frame. This latter option may be preferred in cases where the method is to be applied in real time with image acquisition since the full image sequence will not typically be available at the start of the method.

The machine learning algorithm may be trained in advance based on a training dataset comprising previously acquired image frames of the heart in different of a pre-determined set of phase intervals (each corresponding to a sub-phase of one of systole or diastole phase), and each being manually labelled according to the phase point to which is corresponds. The machine learning algorithm may be a classifier algorithm, adapted to output a classification of an input image frame according to the phase point represented in the image frame.

In one set of embodiments, the machine learning algorithm for determining the phase point may be a spatio-temporal or recurrent neural network (RNN). In this set of embodiments, the input to the algorithm may be the full sequence of image frames. Compared to a classical DNN, for which only the spatial structure of an image is analyzed, RNN and spatio-temporal neural networks are able to analyze temporal relationships between consecutive frames in a sequence.

As noted above, in some examples, the determining of the sub-phase point of each image frame may comprise first detecting within each frame a motion state of one or more anatomical features, each having a cyclical motion pattern over a cardiac cycle, and then determining the phase point based on the detected motion state. In some examples, there may be a separate algorithm for detecting the motion state, followed by an algorithm for detecting the phase point based on the motion state. In some examples, may be an algorithm for detecting the motion state, followed by use of a lookup table to identify the corresponding phase point associated with the detected motion state. In some examples, detection of the motion state may be implicitly performed by a single machine learning algorithm as part of determining the phase point for a given image frame.

In some examples, the determining of the phase point for each image frame may employ use of an ECG signal for the subject. Accordingly, the method 10 may further comprise receiving an ECG signal for the subject, and wherein determining the phase point for each frame is further based on the ECG signal.

The shape of an ECG signal is closely linked with the phases of the cardiac cycle: For instance, the standard QRS pattern always begins immediately before ventricular contraction. Furthermore, the P-wave and the T-wave are related to atrial polarization and ventricle repolarization respectively, and are therefore closely linked to the phases of the heart. Thus, if ECG sensing is available, it may optionally be provided as an additional input to the phase-point determination algorithm, which may improve accuracy of the phase determination, for instance based on identifying the ECG curve patterns described above. For example, a machine learning algorithm may be trained using training data entries which comprise a combination of an input image frame and ECG signal data coinciding with a time point of the frame and wherein each training data entry has been manually tagged with the corresponding phase point for the image frame.

However, the use of ECG is not essential, as the motion of the aortic valve and the surrounding ventricle and atrium is typically sufficient for detection of the phase point, e.g. by a machine learning algorithm.

Once the view represented in the image sequence has been determined and the phase point of each frame in the sequence has been determined, the method comprises applying one or more cardiac valve analysis or assessment algorithms, each algorithm configured to receive one or more input ultrasound frames representative of the heart in a pre-defined one or more views, and at a pre-defined one or more phase points of the cardiac cycle. In some examples, the method may comprise selecting one or more image frames among the sequence of image frames to be provided as an input to at least a subset of the algorithms. At least one suitable frame or sub-sequence of frames may be provided to each assessment algorithm, where suitable means a frame having a view and phase point which matches the input requirements of the relevant algorithm. In some examples, for each frame, a suitable one or more assessment algorithms may be applied. In some examples, one or more of the assessment or analysis algorithms may be adapted to receive as input a sub-sequence of the sequence of image frames, for example a sub-sequence of consecutive image frames spanning a particular sub-phase of the heart cycle.

The assessment or analysis algorithms are each for determining one or more parameters pertaining to a heart valve, for example the aortic or mitral valve. One or more of the algorithms may be adapted to derive a quantitative measure of one or more parameters, such as an area of a heart valve. One or more or the algorithms may be adapted to derive a classification, such as presence or absence of a particular pathological state, or a graded severity of a particular pathological state.

In some embodiments, at least one of the assessment algorithms may be adapted to output an indicator indicative of presence or absence, or a severity of, aortic stenosis (AS). Aortic stenosis means a stenosis of the aortic valve.

In some embodiments, at least one of the assessment algorithms may be adapted to output an indicator indicative of aortic valve area (AVA). AVA computation can be performed directly, e.g. based on image analysis of the imaged aortic valve to estimate a size of the valve. In particular, direct AVA computation can be achieved using a PSAx view of the heart during the end of the systole phase (i.e. when the aortic valve is open. Alternatively AVA may be computed indirectly using the standard AVA continuity equation which requires inputs which include an integral of the time-velocity function of the ejection jet (during systole), and the left ventricular outflow tract (LVOT) diameter. AVA computation using the continuity equation can be performed using a sub-sequence of image frames covering the systole phase, with a PLAx view.

In some embodiments, at least one of the assessment algorithms may be adapted to output an indicator indicative of presence or absence, or a severity of, aortic valve calcification. Aortic valve calcification assessment may require one or more image frames with a PSAx (and optionally PLAx) view at end-diastole.

In some embodiments, at least one of the assessment algorithms may be adapted to output an indicator indicative of mitral valve area.

In some embodiments, at least one of the assessment algorithms may be adapted to output an indicator indicative of a leaflet count of the mitral and/or aortic valve. For example, bicuspid aortic valve is a form of heart disease in which the aortic valve has only two leaflets.

Figure 3:
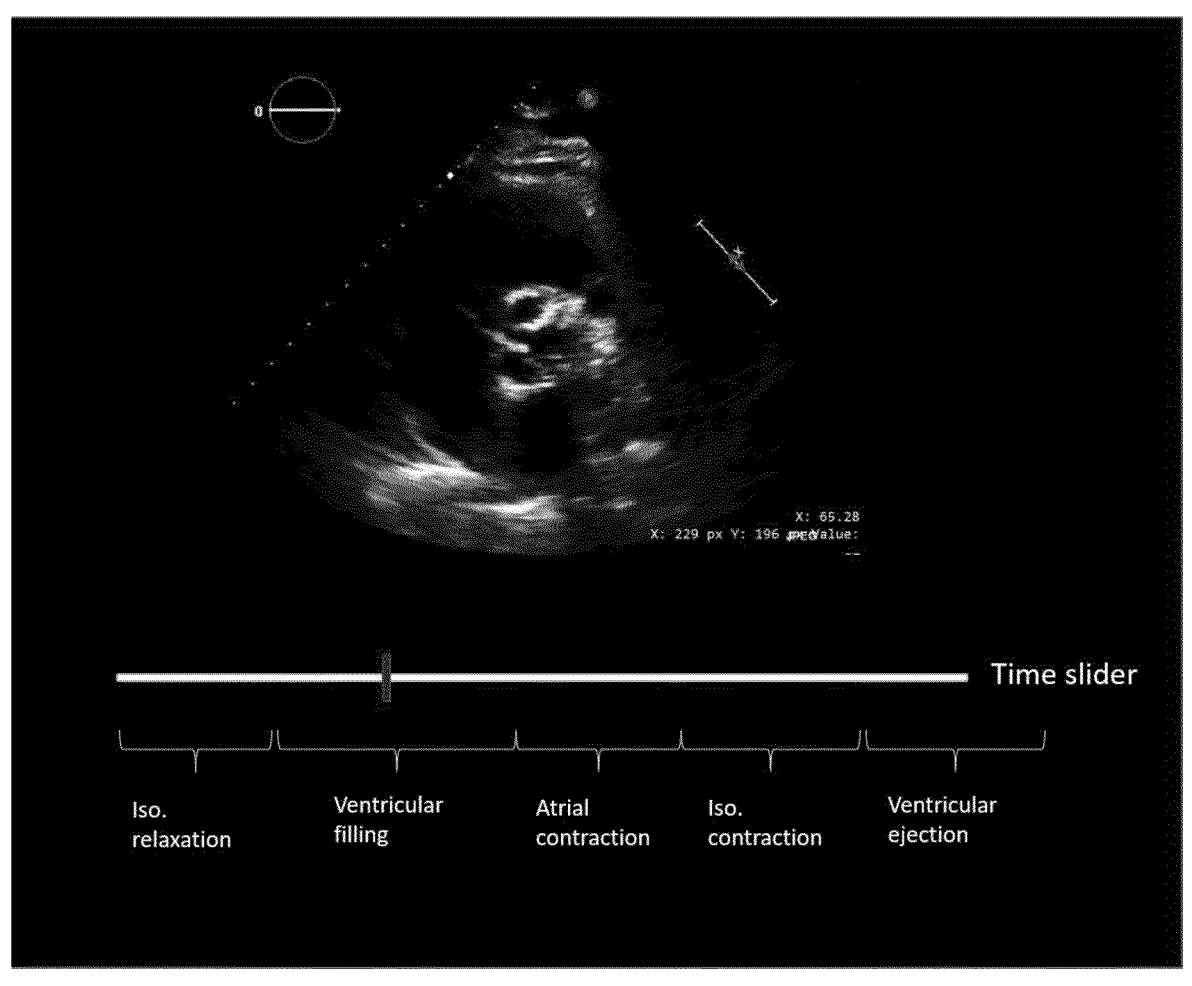
FIG. 3 illustrates a sample display output showing an image frame and detected phase point.

As described above, in one or more embodiments, the method may further comprise generating a display output for causing a user interface to simultaneously display one or more of the image frames and the determined phase point for the frame. In some examples, the user interface may be controlled to provide a user-control permitting selection of a desired phase point during a cardiac cycle, responsive to which an image frame corresponding to the selected phase point is displayed on the display of the user interface. For example, the user interface may display a slider bar having a length, and wherein each selectable position along the slider bar corresponds to a phase point within a full cardiac cycle. Consecutive length sections of the slider bar may be labelled according to the respective phase intervals of the cardiac cycle to which they correspond. An example user interface display output is illustrated in FIG. 3 for example.

Optionally, in some embodiments, the method may further comprise receiving a user input from the user interface indicative of a user modification of the cardiac phase point of one or more of the image frames. Hence here, the user may manually override the automatic phase determinations. The user interface may provide a user control function to permit selection of a given frame and permit entry of an adjusted phase point for the frame.

The user interface may comprise a console having a touch-screen display. Additionally or alternatively, the user interface may comprise a console having a display a further user input means such as a pointer and/or keyboard.

As discussed above, some embodiments of the invention employ use of one or more machine learning algorithms. A machine-learning algorithm is any self-training algorithm that processes input data in order to produce or predict output data.

Suitable machine-learning algorithms for being employed in the present invention will be apparent to the skilled person. Examples of suitable machine-learning algorithms include decision tree algorithms and artificial neural networks. Other machine-learning algorithms such as logistic regression, support vector machines or Naïve Bayesian models are suitable alternatives.

The structure of an artificial neural network (or, simply, neural network) is inspired by the human brain. Neural networks are comprised of layers, each layer comprising a plurality of neurons. Each neuron comprises a mathematical operation. In particular, each neuron may comprise a different weighted combination of a single type of transformation (e.g. the same type of transformation, sigmoid etc. but with different weightings). In the process of processing input data, the mathematical operation of each neuron is performed on the input data to produce a numerical output, and the outputs of each layer in the neural network are fed into the next layer sequentially. The final layer provides the output.

Methods of training a machine-learning algorithm are well known. Typically, such methods comprise obtaining a training dataset, comprising training input data entries and corresponding training output data entries. An initialized machine-learning algorithm is applied to each input data entry to generate predicted output data entries. An error between the predicted output data entries and corresponding training output data entries is used to modify the machine-learning algorithm. This process can be repeated until the error converges, and the predicted output data entries are sufficiently similar (e.g. ±1%) to the training output data entries. This is commonly known as a supervised learning technique.

For example, where the machine-learning algorithm is formed from a neural network, (weightings of) the mathematical operation of each neuron may be modified until the error converges. Known methods of modifying a neural network include gradient descent, backpropagation algorithms and so on.

Embodiments of the invention described above employ a processing arrangement. The processing arrangement may in general comprise a single processor or a plurality of processors. It may be located in a single containing device, structure or unit, or it may be distributed between a plurality of different devices, structures or units. Reference therefore to the processing arrangement being adapted or configured to perform a particular step or task may correspond to that step or task being performed by any one or more of a plurality of processing components, either alone or in combination. The skilled person will understand how such a distributed processing arrangement can be implemented. The processing arrangement includes a communication module or input/output for receiving data and outputting data to further components.

The one or more processors of the processing arrangement can be implemented in numerous ways, with software and/or hardware, to perform the various functions required. A processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A method comprising:

receiving a temporal sequence of ultrasound frames of a heart of a subject, spanning at least one heart cycle;

determining a view represented by the sequence of frames, wherein the view is an imaging view from which the sequence of frames has been acquired;

detecting within each frame a motion state of one or more anatomical features, each having a cyclical motion pattern over a cardiac cycle;

determining for each frame a phase point of the frame within a cardiac cycle, the phase point being a sub-phase point of one of systole or diastole phases, wherein the determining of the phase point of each frame is based on the detected motion state of the one or more anatomical features;

applying one or more cardiac valve analysis algorithms, each algorithm configured to receive one or more input ultrasound frames representative of the heart in a pre-defined one or more views, and at a pre-defined one or more phase points of the cardiac cycle, wherein the one or more input image frames provided to each algorithm are selected based on the determined view and phase point of each of the received frames; and generating a data output representative of an output of each of the one or more algorithms.

2. A method as claimed in claim 1, wherein the phase point corresponds to one of a set of pre-determined phase intervals, each phase interval being a sub-interval of one of systole and diastole phases.

3. A method as claimed in claim 2, wherein the set of pre-determined phase intervals comprise: Isovolumetric relaxation, Ventricular filling, Atrial contraction, Isovolumetric contraction, and Ventricular ejection.

4. A method as claimed in claim 1, wherein determining the view comprises classifying the view as one of a set of pre-defined views, and wherein the set of pre-defined views include one or more of: parasternal short axis (PSAx) view, parasternal long axis (PLAx) view, apical four chamber view, apical two chamber view, or apical long axis view.

5. A method as claimed in claim 1, wherein at least a subset of the one or more analysis algorithms is adapted to output a parameter of the aortic or mitral valve.

6. A method as claimed in claim 1, wherein the one or more analysis algorithms are adapted to output an assessment indicator for one or more of: aortic stenosis (AS), aortic valve area (AVA), aortic valve calcification, mitral valve area, or mitral or aortic valve leaflet count.

7. A method as claimed in claim 1, wherein the method further comprises receiving an ECG signal for the subject, and wherein determining the phase point for each frame is further based on the ECG signal.

8. A method as claimed in claim 1, wherein determining the phase point, and/or determining the view is based on use of an AI algorithm.

9. A method as claimed in claim 8, wherein:

determining the phase point and/or determining the view is based on use of a deep neural network (DNN); and/or determining the phase point is based on use of a recurrent neural network (RNN).

10. A method as claimed in claim 1, further comprising generating a display output for causing a user interface to simultaneously display one or more of the image frames and the determined phase point for the frame.

11. A non-transitory computer-readable storage medium comprising a computer program configured, when executed on a processor, to cause the processor to perform a method as claimed in claim 1.

12. A processing arrangement comprising:

an input/output; and one or more processors adapted to:

receive at the input/output a temporal sequence of ultrasound frames of a heart of a subject, spanning at least one heart cycle;

determine a view represented by the sequence of frames, wherein the view is an imaging view from which the sequence of frames has been acquired;

detect within each frame a motion state of one or more anatomical features, each having a cyclical motion pattern over a cardiac cycle;

determine for each frame a phase point of the frame within a cardiac cycle, the phase point being a sub-phase of one of systole or diastole phases, wherein the determination of the phase point of each frame is based on the detected motion state of the one or more anatomical features;

apply one or more cardiac valve analysis algorithms, each algorithm configured to receive one or more input ultrasound frames representative of the heart in a pre-defined one or more views, and at a pre-defined one or more phase points of the cardiac cycle, wherein the one or more input image frames provided to each algorithm is selected based on the determined view and phase point of each of the received frames; and generate a data output representative of an output of each of the one or more algorithms.

13. A processing arrangement as claimed in claim 12, wherein the phase point corresponds to one of a set of pre-determined phase intervals, each phase interval being a sub-interval of one of systole and diastole phases.

14. A system comprising:

a processing arrangement as claimed in claim 12;

an ultrasound imaging apparatus adapted to output ultrasound image data to the processing arrangement; and a user interface comprising a display, operatively coupled with the processing arrangement.

* * * * *